(12) United States Patent
Kirby et al.

(10) Patent No.: US 7,660,632 B2
(45) Date of Patent: Feb. 9, 2010

(54) METHOD AND APPARATUS FOR HYPOGLOSSAL NERVE STIMULATION

(75) Inventors: Todd Kirby, Spring Church, PA (US); Erik K. Witt, Murrysville, PA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 11/770,202

(22) Filed: Jun. 28, 2007

(65) Prior Publication Data

US 2008/0161877 A1    Jul. 3, 2008

Related U.S. Application Data

(60) Provisional application No. 60/817,907, filed on Jun. 30, 2006.

(51) Int. Cl.
*A61N 1/18* (2006.01)
(52) U.S. Cl. ......................... 607/42; 607/118
(58) Field of Classification Search ......... 607/116–118, 607/42
See application file for complete search history.

(56) References Cited

U.S. PATENT DOCUMENTS

| | | | |
|---|---|---|---|
| 4,830,008 A | 5/1989 | Meer | |
| 5,211,173 A | 5/1993 | Kallok et al. | |
| 5,344,438 A | 9/1994 | Testerman et al. | |
| 5,485,851 A * | 1/1996 | Erickson | 600/529 |
| 5,540,733 A * | 7/1996 | Testerman et al. | 607/42 |
| 5,634,462 A | 6/1997 | Tyler et al. | |
| 6,006,134 A * | 12/1999 | Hill et al. | 607/9 |
| 6,251,126 B1 * | 6/2001 | Ottenhoff et al. | 607/42 |
| 6,456,866 B1 | 9/2002 | Tyler et al. | |
| 6,587,725 B1 * | 7/2003 | Durand et al. | 607/42 |

\* cited by examiner

*Primary Examiner*—Angela D Sykes
*Assistant Examiner*—Joseph Stoklosa

(57) ABSTRACT

A method of treating sleep disordered breathing in a patient includes the steps of monitoring the patient for a pre-inspiratory drive signal indicative of the breathing cycle by sensing electroneurogram activity of a hypoglossal nerve of the patient; and electrically stimulating the hypoglossal nerve of the patient following each detection of the pre-inspiratory drive signal. An implantable apparatus for stimulating a hypoglossal nerve of a patient for the treatment of sleep disordered breathing includes an electrode positioned at least partially around the hypoglossal nerve with a monitoring contact and a stimulation contact and a controller operatively coupled to the monitoring contact and the stimulation contact. The monitoring contact monitors the electroneurogram activity of the hypoglossal nerve for a pre-inspiratory drive signal indicative of the onset of inspiration and sends a signal to the controller which in turn causes the stimulating electrode to electrically stimulate the hypoglossal nerve.

21 Claims, 4 Drawing Sheets

METHOD AND APPARATUS FOR HYPOGLOSSAL NERVE STIMULATION

CROSS-REFERENCE TO RELATED APPLICATIONS

This application claims priority under 35 U.S.C. § 119(e) from provisional U.S. patent application No. 60/817,907 filed Jun. 30, 2007 the contents of which are incorporated herein by reference.

BACKGROUND OF THE INVENTION

1. Field of the Invention

The present invention is related, in general, to a method and apparatus for the treatment of sleep disordered breathing and, more specifically, to a method and apparatus for stimulating the hypoglossal nerve of a patient for the treatment of sleep disordered breathing.

2. Description of the Related Art

Sleep disordered breathing encompasses a number of illnesses including snoring, upper airway resistance syndrome (UARS) and obstructive sleep apnea-hypopnea syndrome (OSAHS). Snoring occurs when there is an obstruction in the back of the mouth which causes these structures to vibrate during breathing. Upper airway resistance syndrome is a disorder that results in an increased resistance to airflow. Obstructive sleep apnea (OSA) results in the partial or complete occlusion of the upper airways of human patients during sleep. In these patients, the upper airways obstruct as often as several times a minute with each episode lasting as long as 20-30 seconds. Each apneic episode ends with a brief arousal from sleep. Consequently, arterial oxyhemoglobin saturation decreases drastically. Complications include excessive daytime sleepiness, restless sleep, morning headache, job-related accidents, impaired short-term memory, polycythema, hypertension, right-sided congestive heart failure, decreased libido, and the like. Personality disorder and other psychological problems may also develop over time. Obstructive sleep apnea is found in 2 to 4 percent of the population, primarily in adult men and post-menopausal women.

In humans, the hypoglossal nerve innervates the intrinsic and extrinsic muscles of the tongue and the geniohyoid muscle. Of these muscles innervated by the hypoglossal nerve, the genioglossus and the geniohyoid muscles are the primary muscles involved in dilating the upper airways (UAWS). Contraction of the genioglossus muscle provides tongue protrusion and, hence, dilates the airways.

It is generally known that the flow of inspired air is doubled by stimulation of the main branch of the hypoglossal nerve. Stimulation of the medial branch is nearly as effective and is superior to stimulation of other branches. Attempts have been made to improve upper airway patency in humans during sleep via direct electrical stimulation of the hypoglossal nerve. For instance, U.S. Pat. No. 4,830,008 to Meer discloses monitoring inspiratory effort followed by stimulation of nerves associated with stimulating the upper airway muscles to treat sleep apnea. The Meer system includes an airway monitor for monitoring inspiratory effort based on sensing "action potentials" in either the diaphragm or phrenic nerve or by sensing negative pressure in the thorax and one or more "effector" electrodes that stimulates the selected upper respiratory muscle nerves.

U.S. Pat. No. 6,587,725 to Durand et al. discloses a method of treating obstructive sleep apnea in a human patient. The method includes the steps of monitoring the human patient for at least partial occlusion of upper airways of the patient associated with obstructive sleep apnea by sensing electroneurogram activity of a hypoglossal nerve of the patient; and, directly electrically stimulating the hypoglossal nerve of the patient when at least partial occlusion of the upper airways of the patient occurs as indicated by the sensed electroneurogram activity of the hypoglossal nerve. A limitation of this method is that it only stimulates the hypoglossal nerve if at least a partial occlusion of the upper airways of the patient occurs. Therefore, this method does not prevent occlusions from occurring.

Other methods of stimulating the hypoglossal nerve include using various physiological variables to synchronize the electrical stimulation with respiration. Hypopharyngeal or espophageal pressure measurements, airflow measurements made with thermistors placed near the nose and mouth, and tracheal inter-ring distance measurements made with a strain gauge are examples of physiological variables that have been investigated for use in synchronization of electrical stimulation of the hypoglossal nerve and/or the genioglossus muscle. For instance, U.S. Pat. No. 5,211,173 to Kallok et al. discloses a method and apparatus for controlling one or more parameters of an electrical stimulation generator used for the treatment of obstructive sleep apnea. Sensors are used to determine the effectiveness of the stimulation. Amplitude and pulse width are modified in response to the measurements from the sensors. However, the method disclosed in this patent and other similar methods have drawbacks and limitations.

Other treatment methods for sleep disordered breathing have included use of a nose mask through which continuous positive airway pressure is applied to keep the upper airways open. This therapy must be continued indefinitely, and only 60-65 percent of these patients can tolerate the technique long-term. Tracheostomy is another treatment for severe sleep disordered breathing, but it is rarely used because of low patient acceptability and relatively high morbidity. Uvulopalatopharyngoplasty, removal of redundant tissue in the oropharynx, and other surgical operations to correct anatomical abnormalities in the upper airways can be considered in certain cases. However, in general, all of the above-mentioned therapies are associated with complications and disadvantages. Weight loss may improve the condition in mild cases, but pharmacologic attempts to treat sleep disordered breathing by increasing pharyngeal muscle activity during sleep have not been found to be effective.

SUMMARY OF THE INVENTION

Therefore, an object of the present invention is to detect a pre-inspiratory drive signal by monitoring the hypoglossal nerve and using that detection as an indication to stimulate the hypoglossal nerve to prevent airway obstruction, rather than waiting for an occlusion within the upper airway to occur before stimulating the hypoglossal nerve. Furthermore, the system of the present invention accomplishes the above described objective without the use of any external sensors.

The present invention is directed to a method of treating sleep disordered breathing in a patient. The method includes the steps of monitoring the patient for a pre-inspiratory drive signal indicative of the breathing cycle by sensing electroneurogram activity of a hypoglossal nerve of the patient; and electrically stimulating the hypoglossal nerve of the patient following each detection of the pre-inspiratory drive signal.

The method may further include amplifying the sensed electroneurogram activity of the hypoglossal nerve to obtain an amplified electroneurogram signal; and using the amplified electroneurogram signal to trigger the direct electrical stimulation of said hypoglossal nerve. The hypoglossal nerve may be monitored continuously for the pre-inspiratory drive signal, and the hypoglossal nerve may be electrically stimulated after a preset period of time elapses from detection of the pre-inspiratory drive signal.

The method may also include sensing a body position of the patient; and initiating monitoring of the patient when the patient is determined to be in a lying down position, or more particularly, a specific lying down position. The specific lying down position may be a supine, prone, or side-lying position.

The method may further include connecting a stimulating nerve electrode to the hypoglossal nerve so that the nerve electrode at least partially encircles the hypoglossal nerve. The stimulating nerve electrode may also include at least first and second contacts and the step of electrically stimulating the hypoglossal nerve comprises passing electrical stimulation pulses between first and second contacts of the nerve electrode and through tissue of the hypoglossal nerve. The electroneurogram activity of the hypoglossal nerve may be sensed with a third contact of the nerve electrode.

The present invention is also directed to a method of stimulating a hypoglossal nerve of a patient for the treatment of sleep disordered breathing. The method includes a first step of monitoring the hypoglossal nerve of the patient. Next, a pre-inspiratory drive signal is detected from the hypoglossal nerve indicative of the breathing cycle. Finally, the hypoglossal nerve is electrically stimulated in response to the detected pre-inspiratory drive signal to prevent occlusion of the patient's upper airway. The pre-inspiratory drive signal is generated by the central nervous system and propagated to the hypoglossal nerve prior to the onset of inspiration.

The present invention is further directed to an implantable apparatus for stimulating a hypoglossal nerve of a patient for the treatment of sleep disordered breathing. The implantable apparatus includes an cuff positioned at least partially around the hypoglossal nerve and having a monitoring contact adapted to sense the electroneurogram activity of the hypoglossal nerve and at least one stimulating contact adapted to electrically stimulate the hypoglossal nerve. The implantable apparatus also includes a controller operatively coupled to the monitoring contact and the stimulation contact device. The monitoring contact monitors the electroneurogram activity of the hypoglossal nerve for a pre-inspiratory drive signal indicative of the onset of the breathing cycle and sends a signal to the controller. The controller operates to cause the stimulating electrode to electrically stimulate the hypoglossal nerve in response to the pre-inspiratory drive signal to prevent occlusion of the patient's upper airway.

The implantable apparatus may further include a position sensing device adapted to determine when the patient is in a lying down position. The position sensing device may be adapted to determine whether the patient is in a supine, prone, or side-lying position. The controller, the monitoring contact of the cuff, the at least one stimulating contact of the cuff, or any combination thereof may be turned off when the position sensing device determines that the patient is in a position other than the lying down position. The position sensing device may be an accelerometer. The implantable apparatus may also further include a wireless communication link associated with the controller for communicating with the controller form outside the patient's body, and a battery for supplying power to the controller and electrode contacts. The battery may also be rechargeable from outside of the body. An amplifier may also be provided for amplifying the pre-inspiratory drive signal.

These and other features and characteristics of the present invention, as well as the methods of operation and functions of the related elements of structures and the combination of parts, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

DETAILED DESCRIPTION OF THE EXEMPLARY EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

The present invention is directed to a system and method for the treatment of sleep disordered breathing through stimulation of the hypoglossal nerve of a human patient. The system and method overcome various shortcomings of prior art systems by monitoring the hypoglossal nerve and stimulating the hypoglossal nerve in response to a pre-inspiratory drive signal before any occlusion of the upper airway of the patient has occurred.

Figure 1:
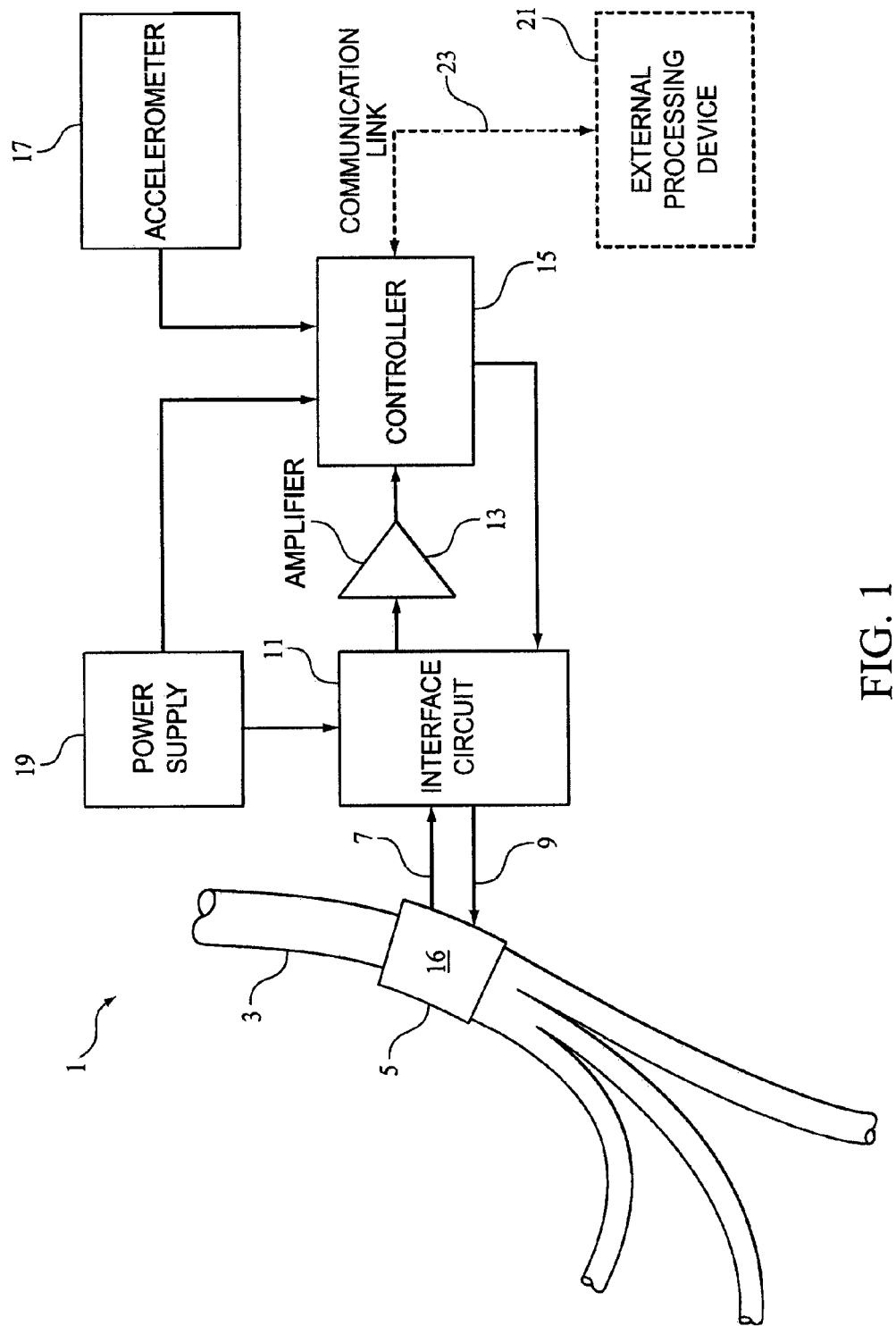
FIG. 1 is a diagrammatic illustration of an implantable apparatus for stimulation of the hypoglossal nerve for the treatment of sleep apnea in accordance with the present invention.
Figure 4:
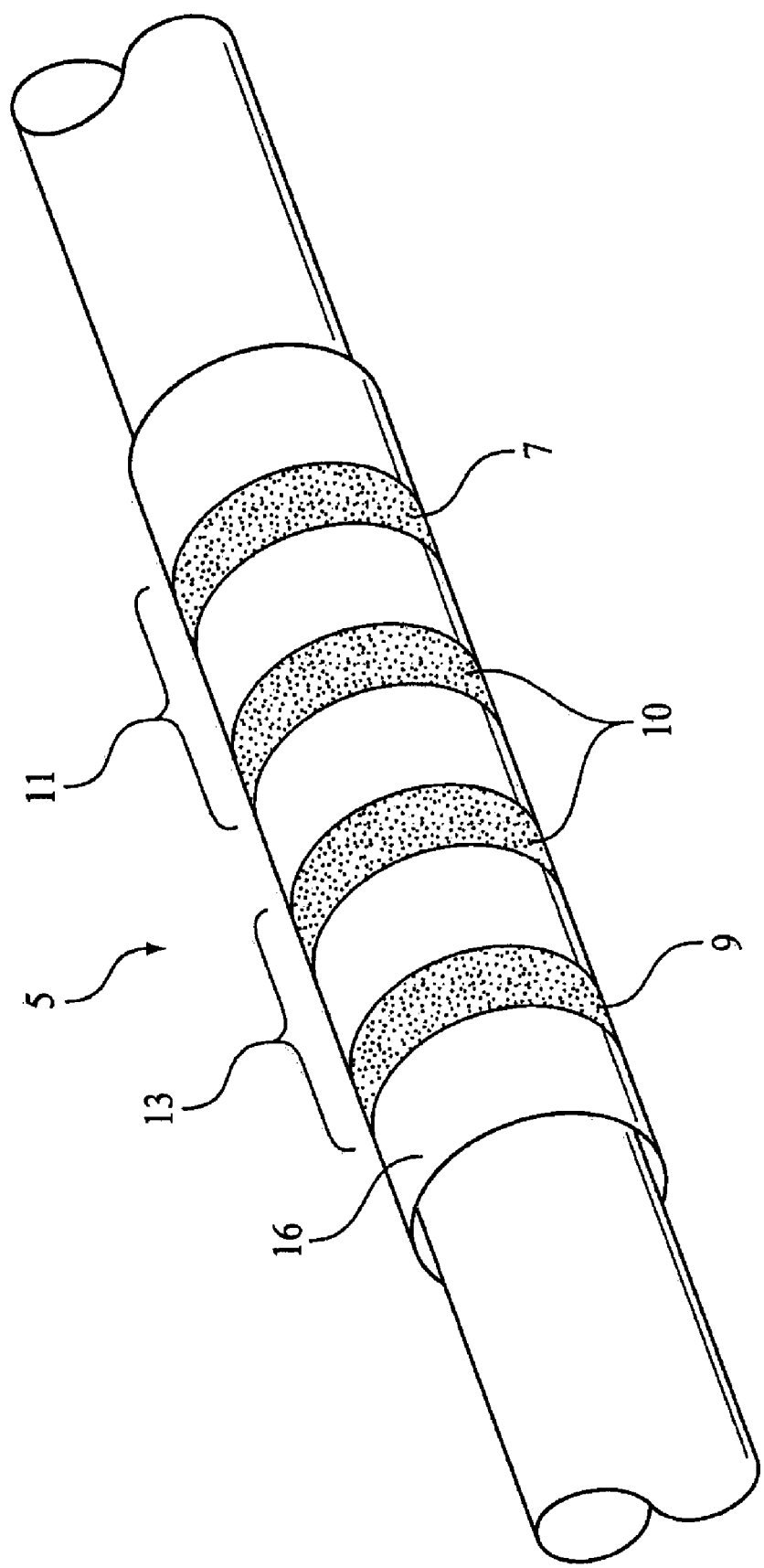
FIG. 4 is a perspective view of the cuff in accordance with the present invention.

With reference to FIGS. 1 and 4, an implantable apparatus 1 for stimulating a hypoglossal nerve 3 of a patient for the treatment of sleep disordered breathing includes an cuff 5 positioned at least partially around hypoglossal nerve 3 and having a monitoring contact 7 adapted to sense the electroneurogram activity of the hypoglossal nerve 3 and a stimulating contact 9 adapted to electrically stimulate the hypoglossal nerve 3. The device further includes at least one ground contact 10 to complete the electrical circuit for monitoring contact 7 and stimulating contact 9. Together, monitoring contact 7 and ground contact 10 forms a monitoring electrode. Similarly, stimulating contact 9 and ground contact 10 forms a stimulating electrode. As shown in FIG. 4, each electrode may have a separate ground contact. Alternatively, both electrodes could utilize the same ground contact. In addition, a single stimulating electrode and a single monitoring electrode are depicted which interface circumferentially about the hypoglossal nerve. However, the present invention contemplates that multiple electrodes could be used for redundancy and/or to target a particular region of the hypoglossal nerve. In another alternative embodiment, the cuff may have one or more monitoring contacts 7 and stimulating contacts 9. However, rather than using a specific ground contact, this embodiment utilizes the cuff body 16 as the ground.

Cuff 5 acts as both hypoglossal nerve stimulation electrode and a hypoglossal nerve activity sensor as described in full detail below. Implantable apparatus 1 is adapted for total implantation in the patient being treated without the need for associated external components. Those of ordinary skill in the art will recognize that cuffs other than the cuff illustrated may be used without departing from the overall scope and intent of the present invention. For instance, the present invention contemplates that the cuff 5 may be U-shaped as disclosed in U.S. Pat. No. 5,344,438. The contents of which are hereby incorporated by reference. However, it can be readily recognized by one of ordinary skill in the art that use of this cuff would require modification to include both a stimulating electrode and a monitoring electrode. Alternatively, the cuff may have a corrugated shape as disclosed in U.S. Pat. No. 5,634,462. The contents of which are hereby incorporated by reference. The cuff may be constructed to have a flat interface as disclosed in U.S. Pat. No. 6,456,866. However, a variety of other electrodes may be used without departing from the scope of the present invention.

As seen in FIG. 1, implantable apparatus 1 further includes an interface circuit 11, an amplifier 13 and a controller 15. Interface circuit 11 receives hypoglossal nerve electroneurogram activity input from monitoring contact 7 of cuff 5 and supplies a hypoglossal nerve activity signal to amplifier 13. Amplifier 13 supplies an amplified and filtered hypoglossal nerve activity signal to controller 15. Controller 15 processes the amplified and filtered hypoglossal nerve activity signal and looks for a pre-inspiratory drive signal. Preferably, the pre-inspiratory drive signal is a spike in the hypoglossal nerve activity signal that is generated by the central nervous system and propagated to the hypoglossal nerve prior to the onset of inspiration. Alternatively, the pre-inspiratory drive signal may be any detectable feature of the electroneurogram activity indicative of the breathing cycle. For instance, the drive signal may be a spike of activity or the absence of activity.

When controller 15 detects the pre-inspiratory drive signal, it outputs a trigger signal to interface circuit 11. Once interface circuit 11 receives the trigger signal, it outputs a stimulation pulse to hypoglossal nerve 3 by way of the stimulating contact 9 of cuff 5. Stimulating contact 9 of cuff 5 includes a first contact and a second contact arranged on hypoglossal nerve 3 to pass electrical stimulation pulses through the tissue of hypoglossal nerve 3. In this manner, implantable apparatus 1 has the ability to stimulate hypoglossal nerve 3 in response to a pre-inspiratory drive signal prior to each breath. Therefore, implantable apparatus 1 prevents occlusions of the upper airway of the patient before such an occlusion has occurred.

Implantable apparatus 1 may further include a position sensing device, such as, but not limited to an accelerometer 17, adapted to determine the body orientation of a patient. Accelerometer 17 is operatively coupled to controller 15 and allows controller 15 to provide different stimulation parameters to be executed based on the position of the patient. Accelerometer 17 determines body orientation of a patient with respect to gravity. Because sleep disordered breathing can be highly dependant on position (supine in particular), in certain patients it may be desirable to intensify the hypoglossal stimulus when the patient is in the supine position. In fact, in certain patients it may be known that sleep disordered breathing is much reduced or not present when lying on the side or front (prone) position, and the stimulation can be reduced or turned off if the patient is in that position. This data would allow for different stimulation parameters to be executed for supine positions versus prone or side sleeping. Accelerometer 17 may also be adapted to terminate therapy when the patient is detected to be upright.

In an alternative embodiment, the use of an accelerometer 17 as the position sensing device allows implantable apparatus 1 to utilize a single sensor assess several parameters that are useful in controlling the therapy delivered by the system. In such an embodiment, accelerometer 17 has a wide bandwidth and is capable of measuring acceleration, motion, and/or vibration from nearly DC, for example, and without limitation, 0 Hz to acoustic frequencies for example, and without limitation, 5-20 kHz. Such an accelerometer 17, allows implantable apparatus 1 to determine physiological parameters such as, but not limited to, body orientation, patient movements, airway vibration and ballistocardiogram.

Body orientation, patient movements and airway vibration can be determined by sampling the relative frequency spectra of the signal (low, medium, and high) produced by accelerometer 17 relative to one another. Generally, low frequency is under about 0.1 Hz. Medium frequency is about 0.1 Hz to about 10 Hz. High frequency is about 10 Hz to about 20 kHz. However, these ranges are only provided as examples and are not intended to limit the present invention. These ranges can be adapted based on the patient being treated. For example, if valuable airway vibration information is contained in lower frequencies, the upper cutoff for patient movements could be reduced.

The four previously mentioned parameters will be specifically discussed hereinafter. Body orientation, as discussed previously, can be determined with respect to gravity through the use of accelerometer 17. Since sleep disordered breathing can be highly dependant on position (supine in particular), in certain patients it may be desirable to intensify stimulation of hypoglossal nerve 3 when the patient is in the supine position. In fact, in certain patients it may be known that sleep disordered breathing is much reduced or not present when on the side or front, and the stimulation can be reduced or turned off if the patient is in that position. This information would allow for different stimulation parameters to be executed for supine positions versus prone or side sleeping. Accelerometer 17 also may be used to provide a signal to controller 15 to terminate therapy when the patient is detected to be upright. In addition, the accelerometer input may be used to control stimulation. For instance, an accelerometer may be used to detect the breathing cycle. Once the breathing rate has been identified, a predictive algorithm may be used to synchronize stimulation with the detected breathing cycle. Of course, as noted above, the stimulation signal may precede or lag the onset of inhalation as deemed appropriate to maximize the therapeutic benefit provided by this device. Use of an accelerometer input may be used as an independent detector to solely monitor breathing. Alternatively, the accelerometer may be used in conjunction with the monitoring electrode to provide a device that monitors both the pre-inspiratory signal and the breathing cycle.

Regarding patient motion, it is well known in the field of actigraphy that patients showing no movement may be considered to be asleep. Accordingly, patient motion, as determined by accelerometer 17, is important in the determination of sleep/wake state, and is thus used to turn on and turn off implantable apparatus 1. Patient motion data may also be communicated to the health care provider via communication link 23 to establish whether implantable apparatus 1 is adequately benefiting the patient.

Regarding airway vibration, airway instability manifests itself as vibration which is transmitted through the soft tissues of the airway and neck. Accelerometer 17 can be configured to detect airway vibrations. The signal produced by accelerometer 17 can be processed in a well-known manner (e.g., total power per unit time and thresholded) by controller 15 to detect an impending, developing or in-progress occlusion or snore. The ability to monitor vibration in the airway via accelerometry can be used together with hypoglossal nerve 3 activity to obtain higher degrees of reliability for proper control of implantable apparatus 1.

Finally, a ballistocardiogram may be part of the signal output by accelerometer 17, and may be extracted therefrom. The ballistocardiogram indicates the beating of the heart, and can be used to provide cardiac parameters such as heart rate, heart rate variability, and certain arrhythmias. These are clinically important because sleep disordered breathing has been shown to cause cardiovascular stress through the sympathetic nervous system activation and intra-thoracic pressure modulation. The frequency spectrum of the ballistocardiogram may overlap one or more of the frequency spectra of the body orientation signal, the patient movement signal or the airway vibration signal. Accordingly, specialized adaptive filters (not shown) may be required to remove the frequency spectrum of the ballistocardiogram from the overlapping spectra from the body orientation signal, the patient movement signal or the airway vibration signal.

While the position sensor has been described hereinabove as an accelerometer, this is not to be construed as limiting, as the use of any suitable position sensing device has been envisioned.

Implantable apparatus 1 also includes a power supply 19 and an external processing device 21. Power supply 19 is desirably a rechargeable battery that is rechargeable from outside of the patient's body via inductive power coil technology. A two-way wireless communication link 23 is associated with controller 15 for communication between controller 15 and external processing device 21. External processing device 21 has the capability of receiving data from controller 15 and transmitting data to controller 15 via communication link 23. In this manner, a clinician can evaluate physiological data accumulated by implantable apparatus 1 and maintenance can be performed thereon. Furthermore, physiological data accumulated by implantable apparatus 1, analyzed data such as, but not limited to, sleep state, and system data such as, but not limited to, charge status and electrode impedance can all be transmitted via communication link 23 to external processing device 21 for further processing and storage on a memory device (not shown) thereof.

Implantable apparatus 1 may further include a titrating subsystem (not shown). The titrating subsystem is an external diagnostic system designed to calibrate implantable apparatus 1. The titrating system may be a separate box that is connected wired or wirelessly to controller 15 of implantable apparatus 1. It may also be integrated into external processing device 21. The titrating subsystem is utilized as prescribed by a clinician to ensure that implantable apparatus 1 achieves adequate levels of stimulation, and to tune up implantable apparatus 1 as the patient's physiology changes due to age or weight loss.

The titrating system may include a variety of sensors to provide additional physiological data. Due to the proximity of hypoglossal nerve 3 to the internal carotid artery and vein, pressure transducers (not shown) can be easily fitted to one or both of these vessels during the same surgical procedure. These pressure transducers may be positioned in close proximity or in direct contact with the vessels for very accurate measurements, or nearby in adjacent tissue. In fact, if implantable apparatus 1 itself is implanted in the neck, the pressure transducer can be incorporated therein, or can be enclosed therein in such a manner that it senses the pressure of the surrounding tissue. A carotid artery sensor (not shown) may be added to provide arterial blood pressure data to the system.

The jugular vein pressure is also physiologically important, and can provide data that closely approximates right atrial pressure. Patients with heart failure may benefit from their clinicians having this data available in disease assessment and management. A pressure sensor (not shown) can be used to measure the beating of the heart, and can be used to provide cardiac parameters such as heart rate, heart rate variability and certain arrhythmias. These are clinically important because sleep disordered breathing has been shown to cause cardiovascular stress through the sympathetic nervous system activation and intra-thoracic pressure modulation.

Pulsus paradoxus (the rise and fall of arterial and venous pressure due to changes in intra-thoracic pressure from breathing) can also be determined with the pressure sensor, and provide to the system as an indication of respiration. This can be useful if the respiratory signal on the hypoglossal nerve is weak, or in determining the temporal relationship of pre-inspiratory signal 23 versus respiration. Wide swings in pulsus paradoxus indicate obstruction (increased negative intrathoracic pressure during inspiration if the airway is obstructed), whereas absent pulsus paradoxus can indicate central apneas. An advantage of using a pressure sensor in the neck is that the sensor can be placed within the same surgical exposure, and does not require intrathoracic placement and running a lead to the stimulator. Importantly, wide swings in pulsus paradoxus can be quantified, and provide an indication of AHI (Apnea Hypopnea Index) or events per unit time to the clinician to indicate therapeutic efficacy.

Figure 2:
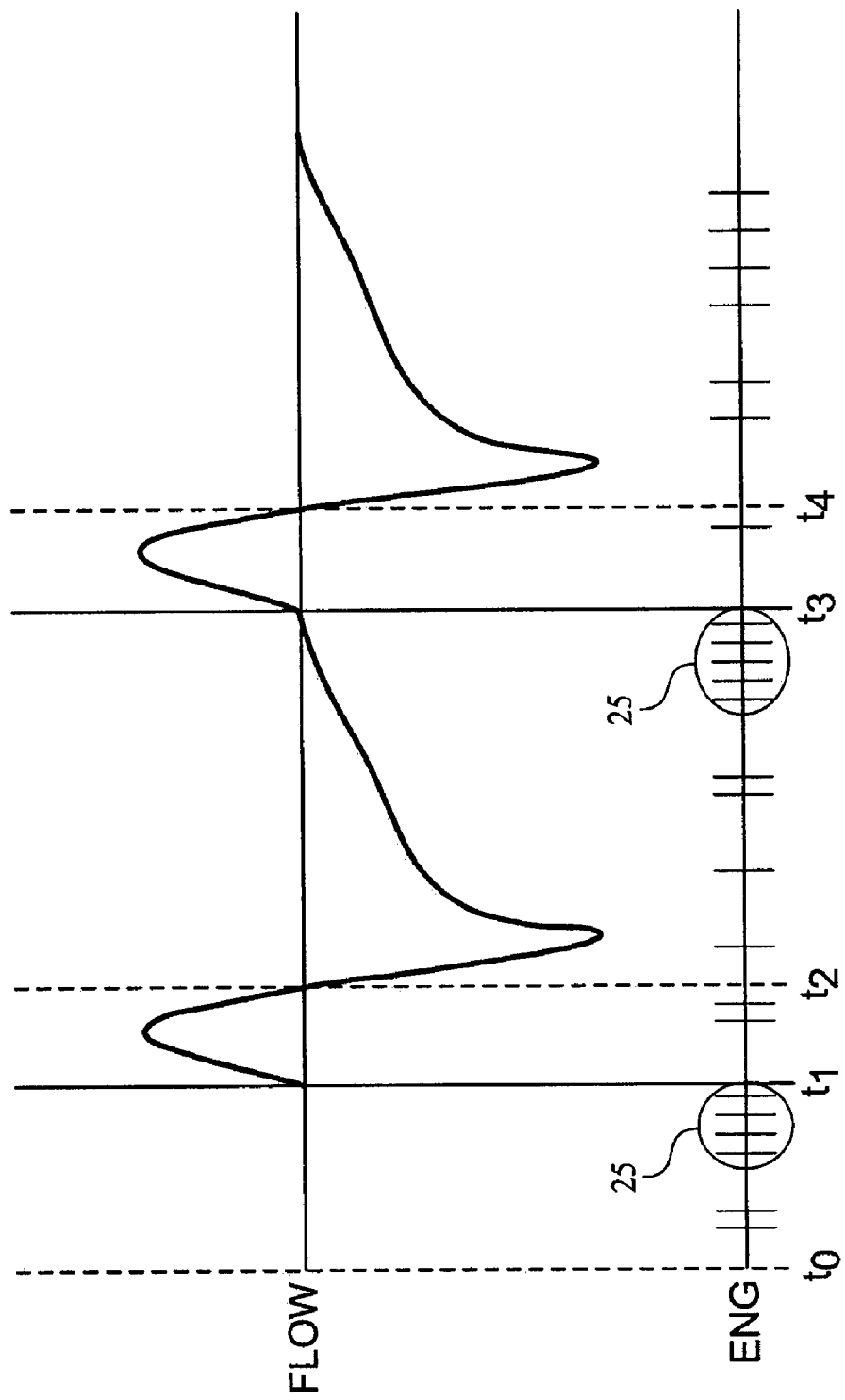
FIG. 2 graphically illustrates the flow of air during a patient's inspiratory cycle and the corresponding electroneurogram activity measured at the hypoglossal nerve.

With reference to FIG. 2 and with continuing reference to FIG. 1, monitoring contact 7 continuously monitors the electroneurogram activity (ENG) of hypoglossal nerve 3 beginning at time $t_0$. Prior to the commencement of the inspiration cycle at time $t_1$, controller 15 detects a pre-inspiratory drive signal 25 from the signals supplied by monitoring electrode 7. Pre-inspiratory drive signal 25 is a spike in the hypoglossal nerve activity signal that is generated by the central nervous system and propagated to the hypoglossal nerve prior to the onset of inspiration. However, the drive signal may be any detectable characteristic of the electroneurogram activity indicative of the breathing cycle. At this point, controller 15 causes stimulating contact 9 of cuff 5 to electrically stimulate hypoglossal nerve 3 in response to the pre-inspiratory drive signal to prevent occlusion of the patient's upper airway. At time $t_2$, the patient's respiratory cycle converts from inhalation to exhalation. Prior to time $t_3$, the first respiratory cycle ends and a pre-inspiratory drive signal 25 signaling the start of a second respiratory cycle is detected. Controller 15 again causes stimulating contact 9 of cuff 5 to electrically stimulate hypoglossal nerve 3 in response to the pre-inspiratory drive signal. At time $t_4$, the second respiratory cycle converts from inhalation to exhalation. Implantable apparatus 1 monitors hypoglossal nerve 3 and stimulates the nerve in response to the detected pre-inspiratory drive signal 25 thereby preventing occlusions in the upper airway of the patient. The controller may monitor the hypoglossal nerve continuously. Alternatively, the controller may monitor the nerve on a periodic basis to conserve energy.

One unique aspect of the present invention is that the controller uses the detected pre-inspiratory signal to control stimulation. As seen in FIG. 2, the breathing cycle and the pre-inspiratory signal are both periodic with substantially the same periodicity. These two signals are out of phase relative to one another. As noted above, the hypoglossal nerve may be stimulated by stimulating the electrode a given time after the pre-inspiratory signal was detected. Ideally, stimulation will coincide with inspiration. However, stimulation may lead or lag the onset of inspiration. Alternatively, the controller may stimulate proximate in time to a subsequent inhalation to provide ample time to process the detected pre-inspiratory signal.

Although the present invention contemplates that a single cuff may be used to both monitor and stimulate a single hypoglossal nerve. The present invention also contemplates using a pair of cuffs on each hypoglossal nerve. One cuff may be used to monitor one hypoglossal nerve while the other cuff may be used to stimulate the other hypoglossal nerve. Alternatively, this invention also contemplates a bilateral system that would utilize a cuff capable of both monitoring and stimulating. A pair of cuffs may be utilizes with one on each hypoglossal nerve. In yet a further alternative, a pair of cuffs may be used on a single nerve with one cuff having the monitoring electrode and the other cuff having the stimulating electrode.

Figure 3:
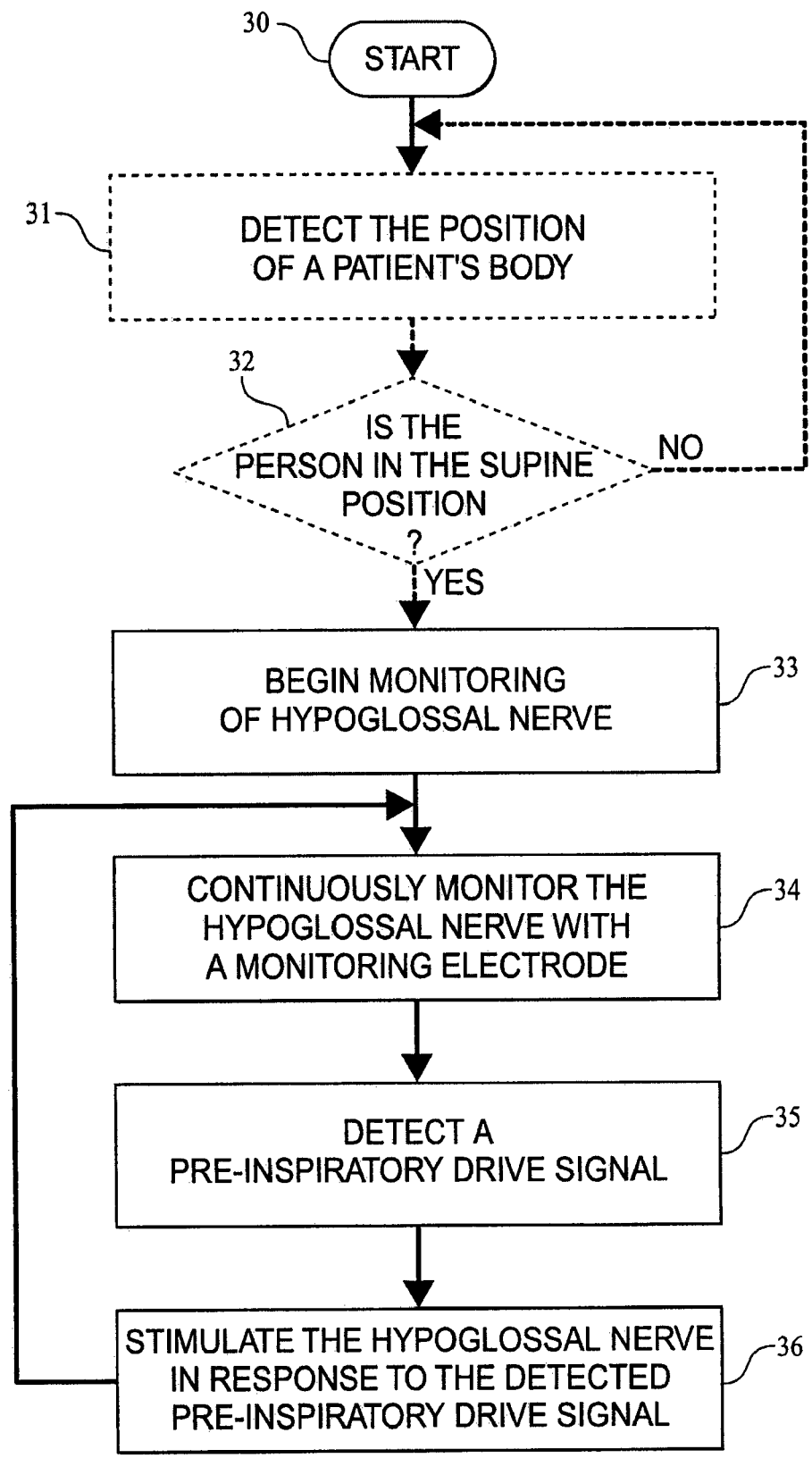
FIG. 3 is a flow-diagram of a method of treating sleep disordered breathing in a patient in accordance with the present invention.

With reference to FIG. 3, and with continuing reference to FIGS. 1 and 2, a flow-diagram illustrating the operation of an implanted implantable apparatus 1 is illustrated. The method commences by advancing from a start step 30 to an optional step 31 wherein accelerometer 17 sends a signal to controller 15. Controller 15 processes the signal to detect the position of the patient's body. At step 32, if the patient is determined to be in the supine position (or alternate selected position or positions), the method advances to step 33. If the patient is determined to be in a different position, the method returns to step 31 and continues to detect the patient's position until the patient is determined to be in the supine position.

Once the patient is found to be in the supine position, controller 15 activates monitoring contact 7 of cuff 5 to begin monitoring hypoglossal nerve 3. Hypoglossal nerve 3 is continuously monitored (step 34) until a pre-inspiratory drive signal (step 35) is detected. At step 36, controller 15 sends a signal to stimulation contact 9 of cuff 5 to stimulate hypoglossal nerve 3 in response to the detected pre-inspiratory drive signal. The method then returns to monitoring step 34 until accelerometer 17 determines that the patient is no longer in the supine position.

Optional activation steps 31 and 32 may be replaced by several different methods for activating implantable apparatus 1. For instance, it is well known in the field of actigraphy that patients showing no movement may be considered to be asleep. This parameter also gives an indication of ambulation. Therefore, patient motion, as determined by accelerometer 17, is important in the determination of sleep/wake state, and is thus used to turn on and turn off implantable apparatus 1. Patient motion data may also be communicated to the health care provider via communication link 23 to establish whether implantable apparatus 1 is adequately benefiting the patient. Alternatively, accelerometer 17 may be utilized to monitor airway vibrations. When airway vibrations are detected due to snoring, for instance, controller 15 can cause implantable apparatus 1 to turn on and begin monitoring hypoglossal nerve 3.

Another method that may be used to initiate monitoring by monitoring contact 9 of cuff 5 is the use of an algorithm to monitor the cyclic nature of the electroneurogram (ENG). Controller 15 learns the pattern of the respiratory cycle based on the ENG obtained from hypoglossal nerve 3. Controller 15 can then use this information to determine when a patient is sleeping and provide a signal to stimulation contact 9 of cuff 5 to begin stimulation of hypoglossal nerve 3 at this time.

While several embodiments of cuff 5 have been described hereinabove, this is not to be construed as limiting the present invention as the use of any suitable electrode for stimulating and monitoring the hypoglossal nerve has been envisioned.

While several embodiments of a hypoglossal nerve stimulation apparatus and methods associated therewith were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method of treating sleep disordered breathing in a patient, comprising:
monitoring the patient for a pre-inspiratory drive signal indicative of the breathing cycle by sensing electroneurogram activity of a hypoglossal nerve of the patient; and
electrically stimulating the hypoglossal nerve of the patient following each detection of the pre-inspiratory drive signal.

2. The method of claim 1, wherein the hypoglossal nerve is electrically stimulated after a preset period of time elapses from detection of the pre-inspiratory drive signal.

3. The method of claim 1, wherein the hypoglossal nerve is monitored continuously for the pre-inspiratory drive signal.

4. The method of claim 1 further comprising:
amplifying the sensed electroneurogram activity of the hypoglossal nerve to obtain an amplified electroneurogram signal; and
using the amplified electroneurogram signal to trigger the direct electrical stimulation of said hypoglossal nerve.

5. The method of claim 1, further comprising:
sensing a body position of the patient; and
initiating monitoring of the patient when the patient is determined to be in a lying down position.

6. The method of claim 5, wherein the lying down position comprises a supine, prone, or side-lying position.

7. The method of claim 1, further comprising connecting a stimulating nerve electrode to the hypoglossal nerve so that the nerve electrode at least partially encircles the hypoglossal nerve.

8. The method of claim 7, wherein the stimulating nerve electrode comprises at least first and second contacts and the step of electrically stimulating the hypoglossal nerve comprises passing electrical stimulation pulses between first and second contacts of the nerve electrode and through tissue of the hypoglossal nerve.

9. The method of claim 7, wherein the electroneurogram activity of the hypoglossal nerve is sensed with a third contact of the nerve electrode.

10. A method of stimulating a hypoglossal nerve of a patient for the treatment of sleep disordered breathing, comprising:

continuously monitoring the hypoglossal nerve of the patient;

detecting a pre-inspiratory drive signal from the hypoglossal nerve indicative of the breathing cycle, the pre-inspiratory drive signal being generated by the central nervous system and propagated to the hypoglossal nerve prior to the onset of inspiration; and electrically stimulating the hypoglossal nerve in response to the detected pre-inspiratory drive signal to prevent occlusion of the patient's upper airway.

11. The method of claim 10, wherein the hypoglossal nerve is electrically stimulated after a preset period of time elapses from detection of the pre-inspiratory drive signal.

12. The method of claim 10, further comprising:
amplifying the detected pre-inspiratory drive signal; and
electrically stimulating the hypoglossal nerve in response to the amplified pre-inspiratory drive signal.

13. The method of claim 12, wherein the pre-inspiratory drive signal is amplified by increasing the frequency, amplitude, or a combination thereof of the detected pre-inspiratory drive signal.

14. The method of claim 12, wherein the amplified pre-inspiratory drive signal triggers the electrical stimulation of said hypoglossal nerve.

15. The method of claim 12, further comprising:
sensing a body position of the patient; and
continuously monitoring of the patient only when the patient is determined to be in a lying down position.

16. The method of claim 15, wherein the lying down position comprises a supine, prone, or side-lying position.

17. The method of claim 10, further comprising connecting a stimulating nerve electrode (5) to the hypoglossal nerve so that the nerve electrode at least partially encircles the hypoglossal nerve.

18. The method of claim 17, wherein the stimulating nerve electrode comprises at least first and second contacts and the step of electrically stimulating the hypoglossal nerve comprises passing electrical stimulation pulses between first and second contacts of the nerve electrode and through tissue of the hypoglossal nerve.

19. The method of claim 18, wherein the monitoring the hypoglossal nerve (3) of the patient comprises monitoring the electroneurogram activity of the hypoglossal nerve with a third contact of the nerve electrode.

20. The method of claim 1, wherein the pre-inspiratory drive signal comprises a signal generated by the central nervous system and propagated to the hypoglossal nerve prior to the onset of inspiration.

21. A method of treating sleep disordered breathing in a patient, comprising:
detecting a pre-inspiratory drive signal by sensing electroneurogram activity of a hypoglossal nerve of the patient, the pre-inspiratory drive signal comprising a signal generated by the central nervous system and propagated to the hypoglossal nerve prior to the onset of inspiration; and
electrically stimulating the hypoglossal nerve of the patient in response to the detection of the pre-inspiratory drive signal.

* * * * *